United States Patent
Imagawa et al.

(10) Patent No.: US 9,919,986 B2
(45) Date of Patent: Mar. 20, 2018

(54) HYDROGENATION SYSTEM FOR AROMATIC COMPOUND, HYDROGEN STORAGE AND TRANSPORTATION SYSTEM EQUIPPED WITH SAME, AND PROCESS FOR HYDROGENATION OF AROMATIC COMPOUND

(71) Applicant: CHIYODA CORPORATION, Yokohama-shi, Kanagawa (JP)

(72) Inventors: Kenichi Imagawa, Yokohama (JP); Hironori Kawai, Yokohama (JP); Masato Shiraga, Yokohama (JP); Yusuke Nakajima, Yokohama (JP)

(73) Assignee: CHIYODA CORPORATION, Kanagawa (JP)

( * ) Notice: Subject to any disclaimer, the term of this patent is extended or adjusted under 35 U.S.C. 154(b) by 0 days.

(21) Appl. No.: 15/116,007

(22) PCT Filed: Jan. 29, 2015

(86) PCT No.: PCT/JP2015/000400
§ 371 (c)(1),
(2) Date: Aug. 2, 2016

(87) PCT Pub. No.: WO2015/115101
PCT Pub. Date: Aug. 6, 2015

(65) Prior Publication Data
US 2017/0166496 A1  Jun. 15, 2017

(30) Foreign Application Priority Data

Feb. 3, 2014  (JP) ................. 2014-018650

(51) Int. Cl.
*C07C 5/10* (2006.01)
*C01B 3/26* (2006.01)
*C01B 3/00* (2006.01)

(52) U.S. Cl.
CPC .............. *C07C 5/10* (2013.01); *C01B 3/0015* (2013.01); *C01B 3/26* (2013.01); *C01B 2203/0277* (2013.01); *C07C 2101/12* (2013.01)

(58) Field of Classification Search
None
See application file for complete search history.

(56) References Cited

U.S. PATENT DOCUMENTS

| 7,132,042 B2 * | 11/2006 | Genetti | .................... | C10G 2/32 |
| | | | | 208/111.35 |
| 2010/0329936 A1 | 12/2010 | Van Wees et al. | | |
| 2014/0364664 A1* | 12/2014 | Chuang | .................... | C07C 5/03 |
| | | | | 585/254 |

FOREIGN PATENT DOCUMENTS

| EP | 1081780 A2 | 3/2001 |
| JP | 2003040601 A | 2/2003 |

(Continued)

OTHER PUBLICATIONS

Extended European Search Report for Application No. 15743150.3, dated Aug. 4, 2017, 6 pages.

*Primary Examiner* — Tam M Nguyen
(74) *Attorney, Agent, or Firm* — Armstrong Teasdale LLP

(57) ABSTRACT

The energy is minimized that is required to lower the concentration of the high boiling point components (containing the poisoning substance for the dehydrogenation catalyst) contained in the hydrogenated aromatic compound produced by the hydrogenation of an aromatic compound. The hydrogenation system (2) for an aromatic compound comprises a hydrogenation reaction unit (11) for adding hydrogen to an aromatic compound by a hydrogenation reaction to produce a hydrogenated aromatic compound, a first separation unit (12) for separating a gas and a liquid component from a product of the hydrogenation reaction unit while maintaining a temperature of the product gener- (Continued)

ally higher than a boiling point of the hydrogenated aromatic compound, and a second separation unit (13) for separating the hydrogenated aromatic compound from the gas component separated by the first separation unit.

5 Claims, 4 Drawing Sheets

(56) References Cited

FOREIGN PATENT DOCUMENTS

| | | | |
|---|---|---|---|
| JP | 2004155730 | A | 6/2004 |
| JP | 2004250255 | A | 9/2004 |
| JP | 2004315380 | A | 11/2004 |
| JP | 2007269522 | A | 10/2007 |
| JP | 2008266315 | A | 11/2008 |
| JP | 4907210 | B2 | 3/2012 |
| JP | 2012526741 | A | 11/2012 |

* cited by examiner

HYDROGENATION SYSTEM FOR AROMATIC COMPOUND, HYDROGEN STORAGE AND TRANSPORTATION SYSTEM EQUIPPED WITH SAME, AND PROCESS FOR HYDROGENATION OF AROMATIC COMPOUND

TECHNICAL FIELD

The present invention relates to a hydrogenation system for an aromatic compound, a hydrogen storage and transportation system incorporated with such a hydrogenation system and a process for the hydrogenation of an aromatic compound, and in particular to a hydrogenation system for an aromatic compound suitable for use in an organic chemical hydride process for storing and transporting hydrogen in the form of a hydrogenated aromatic compound obtained by hydrogenating an aromatic compound.

BACKGROUND OF THE INVENTION

The organic chemical hydride process for hydrogenating aromatic compounds such as toluene has recently been developed for the purposes of storing and transporting hydrogen in the form of hydrogenated aromatic compounds (or organic hydrides). According to this process, hydrogen is converted into a hydrogenated aromatic compound at the site of production, and transported in the form of the hydrogenated aromatic compound. The hydrogenated aromatic compound is separated into the hydrogen and the aromatic compound at a plant or a hydrogen station located near a city or other user of hydrogen by dehydrogenating the hydrogenated aromatic compound. The aromatic compound produced from this dehydrogenation process is transported back to the production site of hydrogen to be hydrogenated by hydrogen once again.

It is known that the catalyst used for the dehydrogenation process is degraded over time by a poisoning substance contained in the hydrogenated aromatic compound (impurities contained in the aromatic compound before being hydrogenated, or impurities produced during the hydrogenation process), and has a limited service life. The kind and the amount of the poisoning substance vary depending on the reaction condition of the hydrogenation process, but most of such substances have higher boiling points than the boiling point of the hydrogenated aromatic compound.

It is also known in a hydrogen storage and transportation system based on the organic chemical hydride process to maintain the concentration of the poisoning substance that is mixed with the hydrogenated aromatic compound (such as methylcyclohexane) in the product of the hydrogenation process by providing a distillation unit following the hydrogenation reaction unit to remove the poisoning substance from the dehydrogenation catalyst and extend the service life of the catalyst. See Patent Document 1.

PRIOR ART DOCUMENT(S)

Patent Document(s)

[Patent Document 1] JP4907210B

SUMMARY OF THE INVENTION

Task to be Accomplished by the Invention

However, according to the prior art disclosed in Patent Document 1, as the distillation unit following the hydrogenation reaction unit is required to process the entire amount of the hydrogenated aromatic compound to remove the poisoning substance from the hydrogenated aromatic compound, the distilling process requires an unacceptably large amount of energy.

The present invention was made in view such a problem of the prior art, and has a primary object to provide a hydrogenation system for an aromatic compound, a hydrogen storage and transportation system incorporated with such a hydrogenation system and a process for the hydrogenation of an aromatic compound which allow the amount of energy that is required to remove the high boiling point components (including the poisoning substance of the dehydrogenation catalyst) mixing with the hydrogenated aromatic compound from the product of the hydrogenation reaction to be minimized.

Means to Accomplish the Task

According to a first aspect of the present invention, the present invention provides a hydrogenation system (2) for an aromatic compound, comprising: a hydrogenation reaction unit (11) for adding hydrogen to an aromatic compound by a hydrogenation reaction to produce a hydrogenated aromatic compound; a first separation unit (12) for separating a gas and a liquid component from a product of the hydrogenation reaction unit while maintaining a temperature of the product generally higher than a boiling point of the hydrogenated aromatic compound; and a second separation unit (13) for separating the hydrogenated aromatic compound from the gas component separated by the first separation unit.

The hydrogenation system for an aromatic compound provided by the first aspect of the present invention is configured to separate the hydrogenated aromatic compound contained in the gas component (or the product in which the concentration of the high boiling point components containing the poisoning substance for the dehydrogenation catalyst is reduced) separated from the liquid component at a temperature generally higher than the boiling point of the hydrogenated aromatic compound so that the energy required to lower the concentration of the high boiling point components that are present with the hydrogenated aromatic compound in the product of the hydrogenation reaction can be minimized.

According to a second aspect of the present invention, in conjunction with the first aspect of the present invention, the hydrogenation system further comprises a cooler (19) for cooling the product from which the gas and liquid components are to be separated by the first separation unit.

The hydrogenation system for an aromatic compound provided by the second aspect of the present invention allows the temperature of the product that is to be separated into the gas and liquid components to be maintained within a desired range in a stable manner in the first separation unit so that the recovering ratio of the gas component (or the product in which the concentration of the high boiling point components containing the poisoning substance for the dehydrogenation catalyst is reduced) separated in the first separation unit and the concentration of the poisoning substance for the dehydrogenation catalyst contained in the gas component can be controlled without any difficulty.

According to a third aspect of the present invention, in conjunction with the first aspect or the second aspect of the present invention, a temperature of the product that is separated by the first separation unit is maintained in a range of 100° C. to 220° C.

The hydrogenation system for an aromatic compound provided by the third aspect of the present invention allows the recovery ratio of the gas component separated by the first separation unit can be increased while lowering the concentration of the poisoning substance for the dehydrogenation catalyst contained in the gas component.

According to a fourth aspect of the present invention, in conjunction with any one of the first to third aspects of the present invention, the hydrogenation system further comprises a distillation unit (51) for distilling the liquid component separated by the first separation unit, wherein an effluent of the distillation unit is mixed with the hydrogenated aromatic compound separated by the second separation unit.

The hydrogenation system for an aromatic compound provided by the fourth aspect of the present invention distills the liquid component (or the product in which the high boiling point components containing the poisoning substance for the dehydrogenation catalyst is concentrated) separated by the first separation unit so that the necessary energy required for the distilling operation can be reduced as compared to the case where the whole amount of the product is distilled. Furthermore, by mixing the effluent (hydrogenated aromatic compound) of the distillation unit with the hydrogenated aromatic compound separated by the second separation unit, the loss of the hydrogenated aromatic compound by being expelled with the poisoning substance for the dehydrogenation catalyst can be minimized.

According to a fifth aspect of the present invention, in conjunction with the fourth aspect of the present invention, the distillation unit performs distillation by using reaction heat of the hydrogenation reaction unit.

The hydrogenation system for an aromatic compound provided by the fifth aspect of the present invention allows the distillation unit to operate by making use of the reaction heat of the hydrogenation reaction unit, and the energy cost for the distillation unit to be thereby minimized.

According to a sixth aspect of the present invention, the present invention provides a hydrogen storage and transportation system (1), comprising: a hydrogenation system (2) for an aromatic compound according to any one of the first to the fifth aspects of the present invention; and a dehydrogenation system (3) for producing hydrogen by a dehydrogenation of the hydrogenated aromatic compound separated by the second separation unit.

The hydrogen storage and transportation system according to the sixth aspect of the present invention, when recirculating an aromatic compound in the hydrogen storage and transportation system, the poisoning substance for the dehydrogenation catalyst is prevented from concentrating in the system without requiring a high energy cost (or extends the life of the dehydrogenation catalyst) so that the supply of hydrogen by the organic chemical hydride method can be maintained over an extended period of time in a stable manner.

According to a seventh aspect of the present invention, the present invention provides a process for hydrogenation of an aromatic compound, comprising: a hydrogenation reaction step for adding hydrogen to an aromatic compound by a hydrogenation reaction to produce a hydrogenated aromatic compound; a first separation step for separating a gas and a liquid component from a product of the hydrogenation reaction unit while maintaining a temperature of the product generally higher than a boiling point of the hydrogenated aromatic compound; and a second separation step for separating the hydrogenated aromatic compound from the gas component separated by the first separation unit while maintaining a temperature of the gas component lower than a boiling point of the hydrogenated aromatic compound.

Effect of the Invention

According to the present invention, the energy required to lower the concentration of the high boiling point components (containing the poisoning substance for the dehydrogenation catalyst) contained in the product of the hydrogenation reaction with the hydrogenated aromatic compound can be minimized.

DETAILED DESCRIPTION OF PREFERRED EMBODIMENT(S)

Preferred embodiments of the present invention are described in the following with reference to the appended drawings.

First Embodiment

Figure 1:
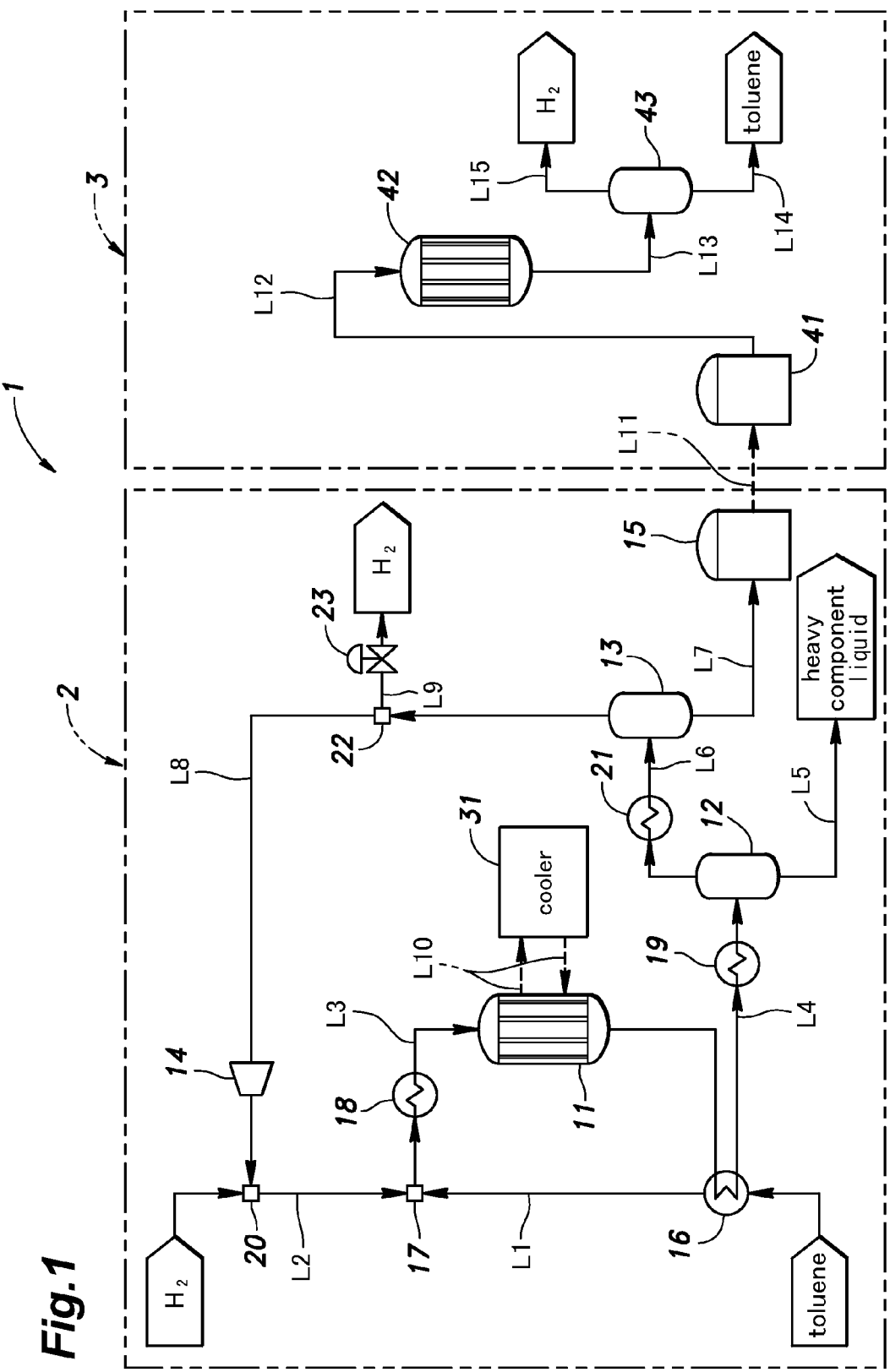
FIG. 1 is a block diagram showing the simplified overall structure of a first embodiment of the hydrogen storage and transportation system according to the present invention.
Figure 2:
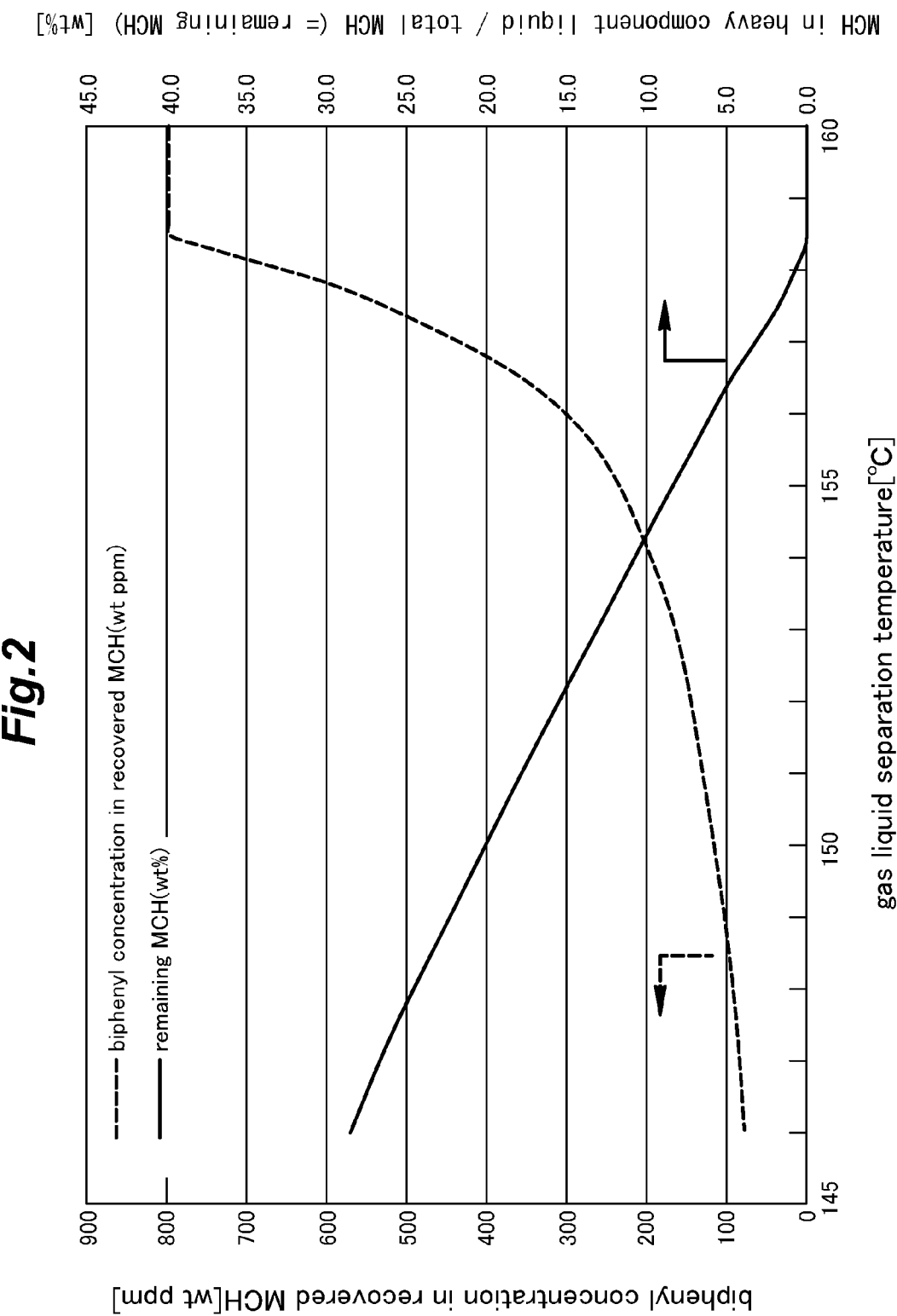
FIG. 2 is a graph showing the relationship between the gas liquid separation temperature and the concentration of the poisoning substance in the methylcyclohexane in the first separation unit, and the relationship between the gas liquid separation temperature and the remaining amount of methylcyclohexane remaining in the heavy component liquid in the liquid form.
Figure 3:
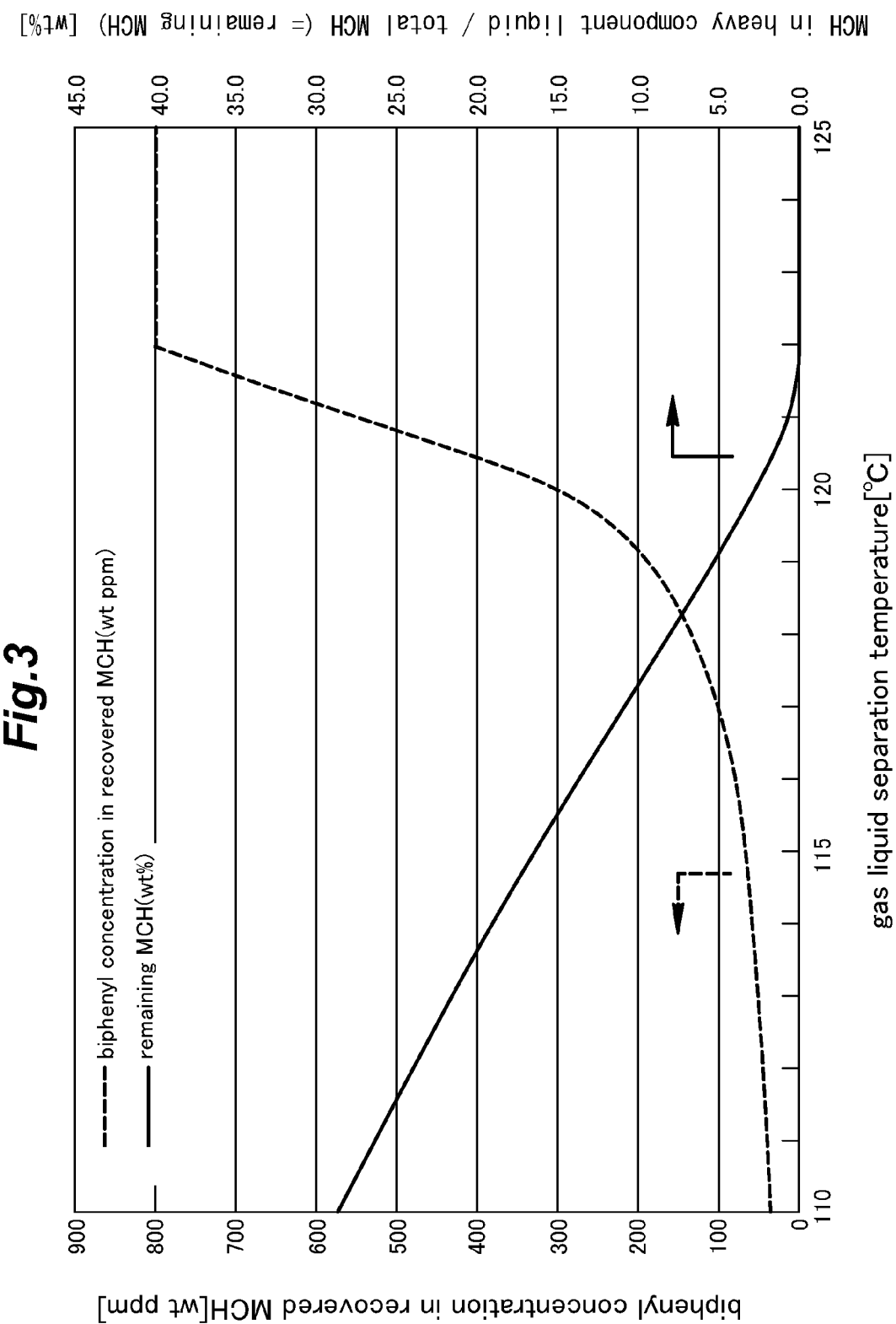
FIG. 3 is a graph similar to the graph of FIG. 2 under a different pressure condition.

FIG. 1 is a block diagram showing the simplified overall structure of a hydrogen storage and transportation system 1 given as a first embodiment of the present invention. FIG. 2 is a graph showing the relationship between the gas liquid separation temperature and the concentration of the poisoning substance (the poisoning substance contained in the final product recovered by the hydrogenation system 2) in the methylcyclohexane in the first separation unit, and the relationship between the gas liquid separation temperature and the remaining amount of methylcyclohexane remaining in the heavy component liquid in the liquid form (a result of a simulation). FIG. 3 is a graph similar to the graph of FIG. 2 under a different pressure condition.

As shown in FIG. 1, the hydrogen storage and transportation system 1 essentially consists of a hydrogenation system 2 for producing a hydrogenated aromatic compound (consisting of methylcyclohexane in this case) by adding hydrogen to an aromatic compound (consisting of toluene in this case) for the purposes of storing and transporting hydrogen, and a dehydrogenation system 3 for producing hydrogen and an aromatic compound by dehydrogenating the hydrogenated aromatic compound.

The hydrogenation system 2 includes a hydrogenation reaction unit 11 for producing methylcyclohexane (MCH) by adding hydrogen to toluene in a hydrogenation reaction, a first separation unit 12 for separating the product of the hydrogenation reaction unit 11 into a gas and a liquid component, a second separation unit 13 for separating the gas component separated by the first separation unit 12 into a gas and a liquid component once again, a transportation unit 14 for recirculating at least a part of the residue (gas component) remaining after MCH (main product) has been separated as the liquid component in the second separation unit 13, and a first storage unit 15 for storing purified MCH (recovered MCH) separated by the second separation unit 13 as the final product of the hydrogenation system 2.

This hydrogenation system 2 receives toluene via an aromatic compound supply line L1 as a reactant of the hydrogenation reaction. The aromatic compound supply line L1 is provided with a preheater 16 for preheating the toluene by exchanging heat with the product of the hydrogenation reaction as will be discussed hereinafter. The hydrogenation system 2 also receives hydrogen via a hydrogen supply line L2 as another reactant of the hydrogenation reaction.

The toluene and the hydrogen are mixed in a merging point 17, and are introduced into the hydrogenation reaction unit 11. Before being introduced into the hydrogenation reaction unit 11, the toluene and the hydrogen are preheated to a prescribed temperature by a preheater 18 provided in a material supply line L3. The preheaters 16 and 18 may consist of any per se known arrangements which are capable of preheating the toluene and the hydrogen to the necessary extent.

In the hydrogenation reaction unit 11, MCH is produced by the hydrogenation reaction between the toluene and the hydrogen (hydrogenation reaction process). The product of the hydrogenation reaction unit 11 is forwarded to a first separation unit 12 via a first product transportation line L4. The product mainly consists of MCH, but contains impurities which may act as a poisoning substance for the dehydrogenation catalyst used in a dehydrogenation reaction unit 42 which will be described hereinafter as well as unreacted residual hydrogen. The first product transportation line L4 is connected to the preheater 16 so that the product is cooled by the heat exchange with the toluene. A first cooler 19 is provided in the first product transportation line L4 downstream of the preheater 16 to further cool the product to a prescribed temperature generally higher than the boiling point of MCH (ideally, strictly higher than the boiling point of MCH). The first cooler 19 may consist of any per se known cooler, be it water-cooled or air-cooled, as long as it is capable of cooling the product to the prescribed temperature. The term "cooler" as used herein should not be interpreted in the narrow meaning thereof, but may cover all sorts of devices that can perform the necessary cooling of the product, including, not exclusively, a temperature control device, a heat transfer device and a heat dissipating device.

The product of the hydrogenation reaction is separated into gas and liquid components in the first separation unit 12 (the first separation process). The first separation unit 12 may consist of a per se known gas-liquid separator, but is characterized in separating the gas and liquid components at a temperature generally higher than the boiling point of MCH (ideally, strictly higher than the boiling point of MCH) and lower than a temperature required for condensing a part of the product. The liquid component (heavy component liquid) separated in the first separation unit 12 includes liquid MCH resulting from partial condensation of the MCH and high boiling point components having higher boiling points than MCH. This heavy component liquid is removed from the final product of the hydrogenation system 2 by being expelled via a heavy component liquid line L5.

The gas component separated in the first separation unit 12 is forwarded to a second separation unit 13 via a second product transportation line L6. The second product transportation line L6 is provided with a second cooler 21. The gas component separated by the first separation unit 12 contains relatively pure MCH free from the heavy component liquid (or the poisoning substance that poisons the dehydrogenation catalyst and is contained in the high boiling component), and after being liquefied in the second cooler 21 (or being cooled to a prescribed temperature lower than the boiling point of MCH), is forwarded to the second separation unit 13. The second separation unit 13 may consist of a per se known gas-liquid separator which separates the gas component from the feed cooled in the second cooler 21 while maintaining the gas component at a temperature lower than the boiling point of MCH (lower than that in the first separation unit 12) (the second separation process). The second separation unit 13 may consist of any per se known gas-liquid separator as long as it is capable of separating MCH in an efficient manner.

The recovered MCH separated as the liquid component by the second separation unit 13 is forwarded to a first storage unit 15 consisting of a storage tank via a first MCH recovery line L7, and is stored therein. Meanwhile, the residual components (unreacted residual hydrogen, byproduct gases, etc.) separated as the gas component are forwarded to a merging point 20 of the hydrogen supply line L2 via a residual gas recirculation line L8 to be mixed with the hydrogen (the recirculation process). Thus, the unreacted residual hydrogen and other residual components are recirculated to the hydrogenation reaction unit 11. The recirculation of the residual components is carried out by a transportation unit 14 provided in the residual gas recirculation line L8. The transportation unit 14 may consist of a per se known compressor for pressurization, but may also consist of any other per se known arrangement providing a similar function.

A gas expulsion unit 22 provided in the residual gas recirculation line L8 is connected to a gas expulsion line L9. In this hydrogenation system 2, the pressure (in particular, the pressure of the residual components in the residual gas recirculation line L8) within the hydrogenation system 2 can be adjusted by controlling a regulator valve 23 provided in the gas expulsion line L9 to expel a part of the residual components to the outside.

Although not shown in the drawings, the hydrogenation reaction unit 11 may consist of a fixed bed, multi-tube reactor of a heat exchanger type, and may have a per se known structure including a plurality of reaction tubes filled with hydrogenation catalyst (solid catalyst) and received in a shell. As will be discussed hereinafter, because the hydrogenation reaction is an exothermic reaction, the reaction heat must be appropriately removed in order to avoid a drop in the conversion rate owing to a rise in the reaction temperature. The shell of the fixed bed, multi-tube reactor is provided with a cooling jacket in which heat medium (such as oil, water and steam) circulates. The heat medium heated by the reaction heat of the hydrogenation reaction is forwarded to a cooling unit 31 via a heat medium circulation line L10, and after being cooled therein, is circulated back to the fixed bed, multi-tube reactor via the heat medium circulation line L10. Owing to this cooling mechanism for the hydrogenation reaction unit 11, the reaction temperature of the hydrogenation reaction is maintained at an appropriate level. When steam is used as the heat medium to be circulated in the heat medium circulation line L10, the heated steam can be industrially utilized for such purposes as heating, humidifying and powering steam engines.

The structure of the hydrogenation reaction unit 11 is not limited to that of the illustrated embodiment, but may also take other forms as long as the required hydrogenation reaction according to the present invention can be achieved. Although not described in any detail, the various lines L1 to L10 in the hydrogenation system 2 may consist of per se known structures including piping, valves and pumps. (The same is true to the lines L12 to L15 of the dehydrogenation system 3 which will be described hereinafter.)

In the hydrogenation reaction unit 11, hydrogen is chemically added to toluene ($C_7H_8$) by the hydrogenation reaction that can be represented by the following chemical equation (1). This hydrogenation reaction is an exothermic reaction ($\Delta H_{298}$=−205 kJ/mol). The toluene is converted into MCH ($C_7H_{14}$).

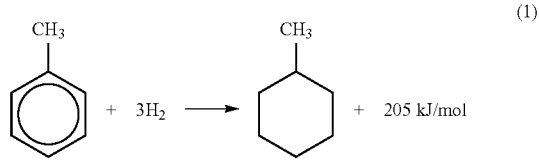

(1)

The reaction temperature for this hydrogenation reaction may be in the range of 150° C. to 250° C., or more preferably in the range of 160° C. to 220° C. The amount of the byproducts (the amount generated by the hydrogenation reaction) remaining in the residue separated from the MCH in the separation unit 13 can be controlled by limiting the rise in the reaction temperature of the hydrogenation reaction. The reaction pressure for this hydrogenation reaction may be in the range of 0.1 MPaG to 5 MPaG, or more preferably in the range of 0.5 MPaG to 3 MPaG. The supply ratio of toluene and hydrogen (toluene/hydrogen mols) to the hydrogenation reaction unit 11 should be stoichiometrically 1/3, but may be in the range of 1/2 to 1/10, or more preferably in the range of 1/2.5 to 1/5, or most preferably in the range of 1/3 to 1/4. A full reaction of toluene can be achieved by optimizing the lower limit of the supply ratio of toluene and hydrogen to the hydrogenation reaction unit 11, and the amount of the gas component that is supplied to the hydrogenation system 2 is prevented from becoming excessive so that the power requirement of the transportation unit 14 can be minimized by optimizing the upper limit of the supply ratio. The excess amount of hydrogen for the given amount of toluene will remain in the residue of the hydrogenation reaction so that the toluene can be fully hydrogenated, and the surplus of hydrogen can be recycled in the subsequent hydrogenation reaction.

In the illustrated embodiment, hydrogen was supplied for the hydrogenation reaction in a pure form for the convenience of the description. However, hydrogen may be mixed with other components to such an extent that the hydrogenation reaction is not obstructed. For instance, instead of pure hydrogen, hydrogen diluted by a prescribed amount of dilution gas (such as methane and nitrogen). For instance, when hydrogen is diluted by methane (possibly also mixed with the residue from the previous reaction including hydrogen and methane), the concentration of methane in the diluted hydrogen for the hydrogenation reaction may be in the range of 5 vol % to 70 vol %, or more preferably in the range of 10 vol % to 30 vol %. In this case, the concentration of hydrogen (which is diluted by methane) may be in the range of 30 vol % to 95 vol %, or more preferably in the range of 70 vol % to 90 vol %.

The aromatic compound that may be used for the hydrogenation reaction in the hydrogenation reaction unit 11 is not limited to toluene, but may also consist of a monocyclic aromatic compound such as benzene and xylene, a bicyclic aromatic compound such as naphthalene and methylnaphthalene, a tricyclic aromatic compound such as anthracene, or a combination of two or more of such aromatic compounds.

The hydrogenated aromatic compound which is the main product of the hydrogenation reaction is produced by hydrogenating any of the aforementioned aromatic compounds, and may consist of a monocyclic hydrogenated aromatic compound such as cyclohexane and methylcyclohexane, a bicyclic hydrogenated aromatic compound such as tetralin, decaline and methyldecaline, a tricyclic hydrogenated aromatic compound such as tetradecahydroanthracene, or a combination of two or more of such hydrogenated aromatic compounds. Such hydrogenated aromatic compounds should be selected from those that are stable liquid under a normal pressure and temperature for the convenience of transportation and storage. When hydrogenated aromatic compounds other than MCH (or aromatic compounds other than toluene) are to be used, the operating condition of the hydrogenation system 2 (the condition for the hydrogenation reaction in the hydrogenation reaction unit 11, the cooling conditions in the first cooler 19 and the second cooler 21, and the temperature conditions in the gas-liquid separation in the first separation unit 12 and the second separation unit 13, etc.) should be varied depending on the particular kind of the hydrogenated aromatic compound that is used.

The hydrogenation catalyst may consist of at least one of active metals selected from a group consisting of nickel (Ni), platinum (Pt), palladium (Pd), rhodium (Rh), iridium (Ir) and ruthenium (Ru) carried by a carrier selected from a group consisting of alumina, silica-alumina and silica, but may also consist of any other per se known catalyst used for hydrogenating an aromatic compound.

The impurities that are produced mainly in the hydrogenation reaction and can be a poisoning substance for the dehydrogenation catalyst include various high boiling component components such as biphenyl (standard boiling point; approximately 256° C.), bicyclohexyl (standard boiling point; approximately 227° C.), 4,4-dimethyl-bicyclohexyl (standard boiling point; approximately 241° C.) and 3,3-dimethyl-bicyclohexyl (standard boiling point; approximately 264° C.). As other impurities that are produced in the hydrogenation reaction and can be a poisoning substance for the dehydrogenation catalyst, in the case where the aromatic compound consists of a monocyclic aromatic compound such as toluene and benzene, there are a polymerization product of a dimer or higher-order oligomer of a six-membered ring compound and a polymerization product of a dimer or higher-order oligomer of a five-membered ring compound. In the case where the aromatic compound consists of a bicyclic aromatic compound such as naphthalene, the impurities may include a polymerization product of a dimer or higher-order oligomer of a bicyclic aromatic compound.

The first separation unit 12 is configured to separate the gas and liquid components from a mixed phase flow (gas-liquid two phase flow) at a high efficiency by making use of the difference in the specific weights. The gas-liquid separation in the first separation unit 12 is aimed at maintaining the concentration of the poisoning substance for the dehydrogenation catalyst contained in the recovered MCH below a required concentration level while maintaining the MCH recovery ratio at the second separation unit 13 at a high level.

In the first separation unit 12, the product of the hydrogenation reaction is separated into the gas and liquid components at a temperature maintained preferably in the range of 100° C. to 220° C. (or a temperature range generally higher than the boiling point of MCH), more preferably in the range of 105° C. to 190° C. or most preferably in the range of 110° C. to 160° C. The optimum temperature range for this gas-liquid separation is determined mostly by (1) the supply ratio of toluene and hydrogen (toluene/hydrogen ratio) that are supplied to the hydrogenation reaction unit 11, (2) the pressure in the reaction vessel of the hydrogenation reaction unit 11 (hydrogenation reaction pressure), and (3) the dilution gas concentration (if the hydrogen is diluted). The toluene/hydrogen ratio and the hydrogenation reaction pressure determine the partial pressure of the MCH at the exit of the reaction vessel of the hydrogenation reaction unit 11 such that the optimum gas-liquid separation temperature becomes higher as the partial pressure of the MCH rises. Also, the optimum gas-liquid separation temperature becomes higher as the hydrogenation reaction pressure rises, and the optimum gas-liquid separation temperature becomes lower as the hydrogenation reaction pressure drops. In particular, the inventors have discovered that the optimum temperature range for this gas-liquid separation is in the range of 100° C. to 220° C. as mentioned above when the hydrogenation reaction pressure is in the range of 0.5 MPaG to 3.0 MPaG.

In the case of the embodiment illustrated in FIG. 2, hydrogen is diluted by nitrogen such that the concentration of nitrogen in the diluted hydrogen is 17 vol %, the toluene/hydrogen ratio is 1/6.6, and the hydrogenation reaction pressure is 2.8 MPaG. Supposing that the poisoning substance for the hydrogenating catalyst consisting of biphenyl is produced in the hydrogenation reaction as shown in FIG. 2, the concentration (wt ppm) of biphenyl in the recovered MCH decreases as the temperature in the first separation unit 12 lowers (or approaches the boiling point of MCH which has a standard boiling point of approximately 101° C.) as indicated by the broken line. Meanwhile, the ratio of the amount of MCH remaining in the heavy component liquid (the remaining amount of MCH remaining in the heavy component liquid in the liquid form) to the total amount of MCH increases as the temperature of the first separation unit 12 lowers. In other words, the changes in temperature of the gas-liquid separation in the first separation unit 12 have mutually opposing influences on the reduction in the concentration of biphenyl in the recovered MCH and the reduction of the remaining amount of MCH in the heavy component liquid. Therefore, in the first separation unit 12, it is necessary to control the reaction temperature so that the concentration of biphenyl in the recovered MCH is kept below a target concentration while the remaining amount of MCH in the heavy component liquid is kept low (below 25 wt %, for instance). The target concentration of the poisoning substance such as biphenyl in the recovered MCH (which may be determined according to the required level of limiting the amount of the poisoning substance for the dehydrogenation reaction) is 500 wt ppm or lower, or more preferably below 100 wt ppm.

In the embodiment illustrated in FIG. 2, in order to keep the amount of the residual biphenyl below 500 wt ppm, the gas-liquid separation temperature should be maintained below 157° C. In particular, in order to keep the amount of the residual biphenyl below the preferred level of 100 wt ppm, the gas-liquid separation temperature is required to be maintained below 149° C. On the other hand, the lower the gas-liquid separation temperature is, the greater the amount of energy required for the recovery of MCH becomes owing to the increase in the remaining amount of MCH in the heavy component liquid (which corresponds to the amount of MCH containing high boiling point components that is supplied to the distillation unit as will be described hereinafter).

When the temperature of the product of the hydrogenation reaction in the first separation unit 12 falls generally below the boiling point of MCH (or below 100° C.) (not shown in FIG. 2), the recovery rate of the gas (recovered MCH) drops sharply owing to the increase in the amount of MCH that is separated as liquid along with the high boiling point components (or the poisoning substance for the dehydrogenation reaction). Therefore, in order to limit the remaining amount of MCH in the heavy component liquid below an acceptable level, the lower limit should be imposed on the gas-liquid separation temperature. The lower limit of the gas-liquid separation temperature may be determined such that the remaining amount of MCH in the heavy component liquid is below 30 wt %, or preferably below 25 wt %.

In the alternate embodiment illustrated in FIG. 3, hydrogen is diluted by nitrogen such that the concentration of nitrogen in the diluted hydrogen is 17 vol %, the toluene/hydrogen ratio is 1/6.2, and the hydrogenation reaction pressure is 1.0 MPaG. In the alternate embodiment illustrated in FIG. 3, in order to limit the amount of residual biphenyl below 500 wt ppm, the gas-liquid separation temperature is required to be maintained below 120° C. In particular, in order to limit the amount of residual biphenyl below 100 wt ppm, the gas-liquid separation temperature is required to be maintained below 117° C. As can be appreciated from the foregoing, the hydrogenation reaction pressure is lowered as compared to the case shown in FIG. 2 so that the optimum operating range of the gas-liquid separation temperature may be shifted to a lower temperature side.

In the illustrated embodiments, only (1) the toluene/hydrogen ratio, (2) the hydrogenation reaction pressure, and (3) the dilution gas concentration were considered as the conditions for dictating the optimum range of the gas-liquid separation temperature, but it is obvious that a person skilled in the art can modify such conditions as required according to the disclosure of this application and the state of the available art. The conditions for the optimum range of the gas-liquid separation temperature are generally applicable without regard to the particular choice of the hydrogenated aromatic compound used in the hydrogenation system 2.

In the illustrated embodiments, the temperature of the product of the hydrogenation reaction in the first separation unit 12 was controlled by adjusting the cooling capacity of the first cooler 19 according to the detected value of a temperature sensor (not shown in the drawings) placed in the first separation unit 12. Thus, the temperature of the product of the hydrogenation reaction in the first separation unit 12 can be controlled within the required temperature range in a stable manner so that the recovery ratio of the gas (or the recovered MCH) in the first separation unit 12 and the concentration of the poisoning substance for the dehydrogenation catalyst contained in the recovered MCH can be controlled without difficulty. If the temperature of the product of the hydrogenation reaction can be controlled within the aforementioned optimum range owing to the heat exchange in the preheater 16 of the first product transportation line L4 and the heat dissipation during transportation alone, the first cooler 19 may be omitted. By providing an additional cooling function (or an additional cooler) to the first separation unit 12, the gas-liquid separation temperature can be controlled either solely by such an additional cooling function or by a combination of such an additional cooling function and the cooler 19.

Because the standard boiling point of MCH which accounts for a large part of the product of the hydrogenation reaction is approximately 101° C., the most part of MCH in the first separation unit 12 is forwarded to the second separation unit 13 via the second product transportation line L6 in the form of gas. On the other hand, because the high boiling point components (including the impurities which may act as the poisoning substance for the hydrogenation catalyst used in a dehydrogenation reaction unit 42 as will be described hereinafter) in the product of the hydrogenation reaction have higher boiling points than the temperature range for the gas-liquid separation in the first separation unit 12, a part of the gaseous MCH is expelled via the heavy component liquid line L5 in the form of liquid (heavy component liquid) along with the condensed liquid MCH.

The dehydrogenation system 3 essentially consists of a second storage unit 41 for storing the recovered MCH, a dehydrogenation reaction unit 42 and a hydrogen separation unit 43 for separating hydrogen and toluene from the product of the dehydrogenation reaction unit 42.

The recovered MCH stored in the first storage unit 15 is forwarded to the second storage unit 41 via a MCH transportation line L11 to be stored therein (the MCH transportation and storage process). The MCH transportation line L11 consists of piping (pipeline or the like) that connects the first storage unit 15 to the second storage unit 41 in this case, but may also consist of other per se known means of transportation (such as tank trucks and tank ships) that can transport MCH from the first storage unit 15 to the second storage unit 41.

The recovered MCH is then forwarded to the dehydrogenation reaction unit 42 via a material supply line L12. The dehydrogenation reaction unit 42 produces mainly hydrogen and toluene from the recovered MCH by means of the dehydrogenation reaction carried out in the presence of the catalyst (dehydrogenation reaction process). The product of the dehydrogenation reaction in the dehydrogenation reaction unit 42 is forwarded to the hydrogen separation unit 43 via a third product recovery line L13. The hydrogen separation unit 43 consists of a per se known gas-liquid separator. In the dehydrogenation reaction unit 42, the reaction product is cooled by a cooling device not shown in the drawings so that the liquefied toluene is separated from the product gas containing hydrogen (hydrogen producing process). The dehydrogenation reaction unit 42 may be immediately followed by a per se known adsorption device for removing the vapor components of toluene and unreacted MCH contained in the product gas. Thereby, the purity of hydrogen in the product gas can be increased.

The separated toluene is forwarded to a storage unit not shown in the drawings via a toluene recovery line L14 to be stored therein. Thereafter, the toluene may be recirculated to the hydrogenation system 2 via a suitable means such as the transportation means for the MCH discussed above. The product gas containing hydrogen is forwarded to a storage unit (such as a high pressure tank) not shown in the drawings via a hydrogen recovery line L15 to be stored therein, and may be transported to the user of hydrogen as required.

The dehydrogenation reaction unit 42 may consist of a fixed bed, multi-tube reactor of a heat exchanger type, and may have a per se known structure including a plurality of reaction tubes filled with dehydrogenation catalyst (solid catalyst) and received in a shell. The recovered MCH is supplied into the reaction tubes, and contacts the catalyst as it flows through the reaction tubes. A heat medium (such as oil, water and steam) of an elevated temperature is supplied into the interior of the shell via a heat transportation line not shown in the drawings so as to heat the recovered MCH and the catalyst by means of heat exchange with the reaction tubes. In the dehydrogenation reaction unit 42, toluene and hydrogen are produced by means of a dehydrogenation reaction which is a reversing of the chemical reaction equation (1) discussed above.

The dehydrogenation catalyst may consist of at least one of active metals selected from a group consisting of nickel (Ni), platinum (Pt), palladium (Pd), rhodium (Rh), iridium (Ir) and ruthenium (Ru) carried by a carrier (for instance, highly porous γ-alumina having a surface area greater than 150 m$^2$/g, a pore volume greater than 0.40 cm$^3$/g and an average pore diameter of 90 to 300 Angstrom, with the pores with diameters in the range of ±30 Angstrom of the average pore diameter accounting for 50% or more of the total pore volume) selected from a group consisting of alumina, silica-alumina and silica, but may also consist of any other per se known catalyst used for dehydrogenating a hydrogenated aromatic compound.

In the dehydrogenation reaction unit 42, the poisoning substance for the dehydrogenation catalyst contained in the recovered MCH has a tendency to be deposited on the dehydrogenation catalyst during the course of dehydrogenation so that a coking reaction which is detrimental to the catalyst activity inevitably occurs. However, in the hydrogen storage and transportation system 1 described above, because the concentration of the high boiling point components (the poisoning substance for the dehydrogenation catalyst) contained in the recovered MCH are reduced in the hydrogenation system 2 in advance, the poisoning of the dehydrogenation catalyst in the dehydrogenation system 3 is minimized. In particular, in this hydrogen storage and transportation system 1, because the gas component (or the product in which the concentration of the high boiling point components containing the poisoning substance for the dehydrogenation catalyst is reduced) which is separated from the liquid component at a temperature generally higher than the boiling point of MCH (ideally, strictly higher than the boiling point of MCH) (hydrogenated aromatic compound) in the first separation unit 12 of the hydrogenation system 2 is further separated as a gas component at a temperature lower than the boiling point of MCH (lower than the temperature in the first separation unit 12) in the second separation unit 13, the energy required to lower the concentration of the high boiling point components (the poisoning substance for the dehydrogenation catalyst) can be minimized.

The storage of a hydrogenated aromatic compound (or the organic hydride) and the production of hydrogen from the hydrogenated aromatic compound in this hydrogen storage and transportation system 1 may be performed by an organic chemical hydride method.

For the details of the organic chemical hydride method, reference may be made to "Development of Dehydrogenation Catalyst for Organic Chemical Hydride Method" by Yoshimi OKADA, et al., *Catalysts & Catalysis*, 2004, 46 (6), p 510-512, ISSN 05598958, "Dehydrogenation Catalyst Development for Organic Chemical Hydride Method and Hydrogen Energy Chain Vision", by Yoshimi OKADA, et al., *Catalysts & Catalysis*, 2009, 51 (6), p 496-498, ISSN 05598958, "Development of Dehydrogenation Catalyst for Organic Chemical Hydride Method with the Aim to Establish a Mass, Long-Distance Storage and Transportation Technology of Hydrogen Energy" by Yoshimi OKADA, et al., *Chemical Engineering*, 2010, 74 (9), p 468-470, ISSN 03759253, and "Development of Dehydrogenation Catalyst for Organic Chemical Hydride Method in Hydrogen Storage and Transportation (New Year Special Edition, GCS Symposium 2005)", by Yoshimi OKADA, et al., *Fine Chemical*, 2006, 35 (1), p 5-13, in lieu of a detailed discussion in this application.

Second Embodiment

Figure 4:
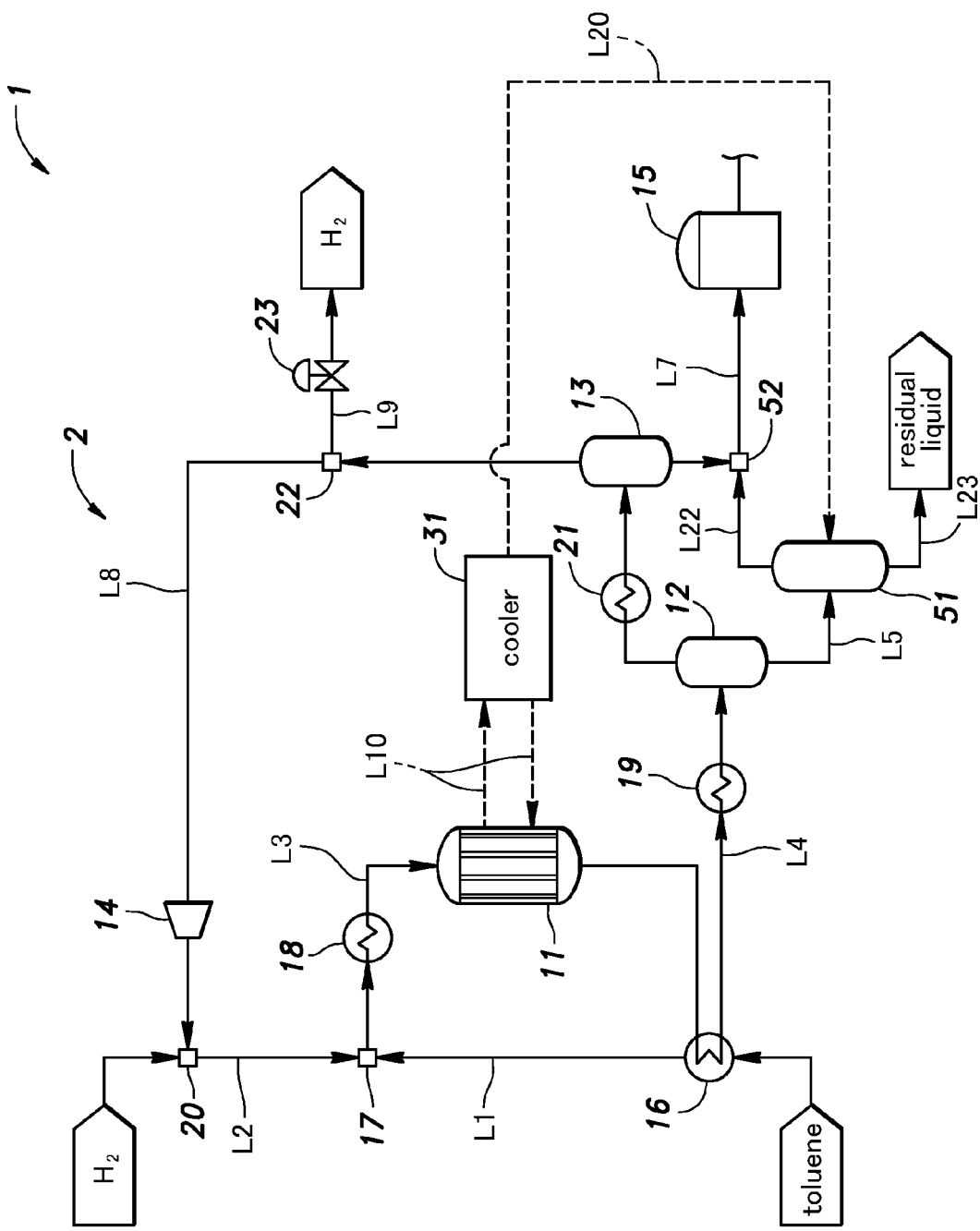
FIG. 4 is a block diagram showing the simplified overall structure of a second embodiment of the hydrogen storage and transportation system according to the present invention.

FIG. 4 is a block diagram showing the simplified overall structure of a hydrogen storage and transportation system 1 given as a second embodiment of the present invention. In FIG. 4, the parts corresponding to those in the first embodiment are denoted with like numerals, and the dehydrogenation system 3 is omitted from the illustration. The second embodiment is similar to the first embodiment except for the matters discussed in the following.

The hydrogen storage and transportation system 1 of the second embodiment differs from that of the first embodiment in that a distillation unit 51 is provided on the downstream end of the first separation unit 12 of the hydrogenation system 2, and the reaction heat of the hydrogenation reaction unit 11 is used by the distillation unit 51.

In this hydrogenation system 2, the liquid (heavy component liquid) separated by the first separation unit 12 is supplied to the distillation unit 51 via a heavy component liquid expulsion line L5. The distillation unit 51 may consist of a per se known distillation tower having three to eight trays or plates which provides a distillation efficiency of 50% or more by performing a distillation operation of two to four theoretical plates. MCH of a high purity can be obtained from the top vapor fraction of the distillation tower. The ratio of the MCH that is recovered by the distillation unit 51 is 80 to 99 wt % of the heavy component liquid that is supplied to the distillation unit 51. The MCH that is recovered by the distillation unit 51 is conducted along a second MCH recovery line L22 which merges with the first MCH recovery line L7 at a merging point 52 to be mixed with the recovered MCH that is supplied by the second separation unit 13. Meanwhile, the residual liquid (residue) of the distillation unit 51 in which the impurities acting as the poisoning substance for the dehydrogenation catalyst are expelled via a residual liquid expulsion line L23 so as to be removed from the recovered MCH of the hydrogenation system 2. The amount of the residual liquid is approximately 1 wt % to 20 wt % of the residual liquid that is supplied to the distillation unit 51.

The distillation unit 51 is provided with a heater (not shown in the drawings) to heat the supplied material (heavy component liquid), and the heater receives at least a part of the heat medium (steam in this case) which is heated by the reaction heat of the hydrogenation reaction in the hydrogenation reaction unit 11 and forwarded thereto from the cooling unit 31 via a heat medium supply line L20. Thereby, the cost of energy in the distillation unit 51 can be minimized. The distillation unit 51 may consist of any per se known device as long as it is at least capable of extracting highly pure MCH (in which the concentration of impurities that can act as the poisoning substance for the dehydrogenation catalyst is less than 100 wt ppm). If applicable, the distillation operation may be performed as a simple distillation. The reaction heat of the hydrogenation reaction may also be used for heating a reboiler and/or directly heating the distillation tower, in addition to acting as a heat source for the heater.

Thus, in the hydrogenation system of the second embodiment, the liquid separated by the first separation unit 12 (the product in which high boiling point components that can act as the poisoning substance for the dehydrogenation catalyst is concentrated) is distillated, instead of distilling the entire amount of the product, so that the energy required for the distillation can be minimized. In the hydrogenation system 2 of the second embodiment, the effluent of the distillation unit 51 (highly pure MCH) is mixed with the liquid (recovered MCH) separated by the second separation unit 13 so that the amount of MCH that is removed along with the poisoning substance for the dehydrogenation catalyst can be minimized (or, in other words, the recovery ratio of the recovered MCH can be improved).

The present invention has been described in terms of the concrete embodiments thereof which were given only as examples, and should not be interpreted as limiting the present invention. The various components of the hydrogenation system for an aromatic compound, the hydrogen storage and transportation system incorporated with such a hydrogenation system and the process for the hydrogenation of an aromatic compound according to the present invention discussed above can be partly substituted and omitted without departing from the spirit of the present invention. Also, some of the various components of the embodiments discussed above may be combined into a composite unit combining a plurality of functionalities.

LIST OF THE NUMERALS

1 hydrogen storage and transportation system
2 hydrogenation system
3 dehydrogenation system
11 hydrogenation reaction unit
12 first separation unit
13 second separation unit
15 first storage unit
19 first cooler
41 second storage unit
42 dehydrogenation reaction unit
43 hydrogen separation unit
51 distillation unit

The invention claimed is:

1. A hydrogenation system for an aromatic compound, comprising:
  a hydrogenation reaction unit in which hydrogen is added to an aromatic compound by a hydrogenation reaction to produce a hydrogenated aromatic compound;
  a first separation unit connected with the hydrogenation reaction unit to receive a product of the hydrogenation reaction unit, the first separation unit separating a gas component and a liquid component from the product of the hydrogenation reaction unit while maintaining a temperature of the product generally higher than a boiling point of the hydrogenated aromatic compound such that the gas component contains the hydrogenated aromatic compound; and
  a second separation unit connected with the first separation unit to receive the gas component separated by the first separation unit, the second separation unit separating the hydrogenated aromatic compound from the gas component separated by the first separation unit,
  wherein the hydrogenation system further comprises a distillation unit connected with the first separation unit to receive the liquid component separated by the first separation unit, the distillation unit distilling the liquid component separated by the first separation unit such that an effluent of the distillation unit contains the hydrogenated aromatic compound, wherein the effluent of the distillation unit is mixed with the hydrogenated aromatic compound separated by the second separation unit.

2. The hydrogenation system for an aromatic compound according to claim 1, further comprising a cooler configured to cool the product from which the gas and liquid components are to be separated by the first separation unit.

3. The hydrogenation system for an aromatic compound according to claim 1, wherein a temperature of the product that is separated by the first separation unit is maintained in a range of 100° C. to 220° C.

4. The hydrogenation system for an aromatic compound according to claim 1, wherein the distillation unit performs distillation by using reaction heat of the hydrogenation reaction unit.

5. A hydrogen storage and transportation system, comprising:
  the hydrogenation system for an aromatic compound according to claim 1; and
  a dehydrogenation system in which hydrogen is produced by a dehydrogenation of the hydrogenated aromatic compound separated by the second separation unit mixed with the effluent of the distillation unit.

* * * * *